US009072588B2

(12) United States Patent
Böhm et al.

(10) Patent No.: US 9,072,588 B2
(45) Date of Patent: Jul. 7, 2015

(54) SELECTABLE VARIED CONTROL VALVE SYSTEMS FOR IOP CONTROL SYSTEMS

(75) Inventors: Sebastian Böhm, San Diego, CA (US); Leslie A. Field, Portola Valley, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 809 days.

(21) Appl. No.: 13/251,368

(22) Filed: Oct. 3, 2011

(65) Prior Publication Data
US 2013/0085440 A1    Apr. 4, 2013

(51) Int. Cl.
*A61F 9/00*    (2006.01)
*A61F 9/007*    (2006.01)

(52) U.S. Cl.
CPC .................. *A61F 9/00781* (2013.01)

(58) Field of Classification Search
USPC ............ 604/8–10, 93.01, 104, 171, 246, 514, 604/521, 19, 21, 294, 298, 890.1, 891.1, 604/892.1, 30, 99.02; 424/427; 128/887, 128/898
See application file for complete search history.

(56) References Cited

U.S. PATENT DOCUMENTS

| | | | |
|---|---|---|---|
| 4,089,329 A | 5/1978 | Couvillon, Jr. et al. | |
| 4,206,762 A | 6/1980 | Cosman | |
| 4,457,757 A | 7/1984 | Molteno | |
| 4,560,375 A | 12/1985 | Schulte et al. | |
| 4,750,901 A | 6/1988 | Molteno | |
| 4,922,913 A | 5/1990 | Waters et al. | |
| 5,005,577 A | 4/1991 | Frenkel | |
| 5,178,604 A | 1/1993 | Baerveldt | |
| 5,179,953 A | 1/1993 | Kursar | |
| 5,397,300 A | 3/1995 | Baerveldt | |
| 5,433,701 A | 7/1995 | Rubinstein | |
| 5,476,445 A | 12/1995 | Baerveldt | |
| 5,558,629 A | 9/1996 | Baerveldt | |
| 6,447,449 B1 | 9/2002 | Fleischman et al. | |

(Continued)

FOREIGN PATENT DOCUMENTS

| | | |
|---|---|---|
| DE | 4438201 | 5/1996 |
| EP | 2427097 | 3/2012 |

(Continued)

OTHER PUBLICATIONS

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

(Continued)

*Primary Examiner* — Tan-Uyen (Jackie) T Ho
*Assistant Examiner* — Mark Wardas
(74) *Attorney, Agent, or Firm* — Haynes and Boone, LLP (57) ABSTRACT

A selectable IOP valve for implantation in an eye of a patient controls IOP and/or bleb pressure. The valve includes a drainage tube configured to convey aqueous from an anterior chamber of an eye and includes a selectable flow control valve in fluid communication with the drainage tube and configured to control flow rates of the aqueous. The valve system includes a plurality of flow control pathways arranged to operate in parallel with each other, each of the flow control pathways being in communication with an entry port to the valve system. A flow control mechanism controls aqueous flow through the pathways. Methods and systems are also disclosed.

44 Claims, 5 Drawing Sheets

(56) References Cited

U.S. PATENT DOCUMENTS

| | | | |
|---|---|---|---|
| 6,579,235 B1 | 6/2003 | Abita et al. | |
| 6,589,198 B1 | 7/2003 | Soltanpour et al. | |
| 6,712,764 B2 | 3/2004 | Jeffries et al. | |
| 6,749,568 B2 | 6/2004 | Fleischman et al. | |
| 6,939,299 B1 | 9/2005 | Petersen et al. | |
| 7,137,952 B2 | 11/2006 | Leonardi et al. | |
| 7,169,106 B2 | 1/2007 | Fleischman et al. | |
| 7,252,006 B2 | 8/2007 | Tai et al. | |
| 7,354,416 B2 | 4/2008 | Quiroz-Mercado et al. | |
| 7,409,863 B2 | 8/2008 | Bateman et al. | |
| 7,612,328 B2 | 11/2009 | Kaiser | |
| 8,333,874 B2 * | 12/2012 | Currie | 204/403.01 |
| 2001/0000527 A1 | 4/2001 | Yaron et al. | |
| 2002/0143284 A1 | 10/2002 | Tu et al. | |
| 2002/0193674 A1 | 12/2002 | Fleischman et al. | |
| 2003/0078487 A1 | 4/2003 | Jeffries | |
| 2003/0225318 A1 | 12/2003 | Montegrande et al. | |
| 2004/0059248 A1 | 3/2004 | Messner et al. | |
| 2004/0073137 A1 | 4/2004 | Lloyd et al. | |
| 2004/0116794 A1 | 6/2004 | Fink | |
| 2004/0254438 A1 | 12/2004 | Chuck et al. | |
| 2004/0254517 A1 * | 12/2004 | Quiroz-Mercado et al. | 604/8 |
| 2005/0159660 A1 | 7/2005 | Montegrande et al. | |
| 2005/0271704 A1 * | 12/2005 | Tu et al. | 424/427 |
| 2005/0273033 A1 | 12/2005 | Grahn et al. | |
| 2007/0109117 A1 | 5/2007 | Heitzmann et al. | |
| 2007/0123767 A1 | 5/2007 | Montegrande et al. | |
| 2007/0129623 A1 | 6/2007 | Fleischman et al. | |
| 2008/0015421 A1 | 1/2008 | Penner | |
| 2008/0129486 A1 | 6/2008 | Jeckelmann et al. | |
| 2008/0228127 A1 | 9/2008 | Burns et al. | |
| 2009/0069648 A1 | 3/2009 | Irazoqui et al. | |
| 2009/0076367 A1 | 3/2009 | Sit et al. | |
| 2009/0227933 A1 | 9/2009 | Karageozian | |
| 2009/0275924 A1 | 11/2009 | Lattanzio et al. | |
| 2010/0010416 A1 | 1/2010 | Juan, Jr. et al. | |
| 2010/0042209 A1 | 2/2010 | Guarnieri | |
| 2010/0121348 A1 | 5/2010 | Van Der Burg et al. | |
| 2010/0234717 A1 | 9/2010 | Wismer | |
| 2010/0249691 A1 * | 9/2010 | Van Der Mooren et al. | 604/9 |
| 2010/0253167 A1 | 10/2010 | Charnley | |
| 2011/0071458 A1 | 3/2011 | Rickard | |
| 2011/0071459 A1 | 3/2011 | Rickard | |
| 2011/0071505 A1 * | 3/2011 | Rickard et al. | 604/540 |
| 2012/0283669 A1 * | 11/2012 | Coldren et al. | 604/294 |

FOREIGN PATENT DOCUMENTS

| | | |
|---|---|---|
| WO | 93/03665 | 3/1993 |
| WO | WO 98/03665 | 4/1993 |
| WO | 03/001991 | 1/2003 |
| WO | WO 03/102632 | 12/2003 |
| WO | 2007/136993 | 11/2007 |
| WO | 2009/026499 | 2/2009 |
| WO | 2009/049686 | 4/2009 |
| WO | WO 2009/081031 | 7/2009 |
| WO | 2010/136071 A1 | 12/2010 |
| WO | 2013/052332 A1 | 4/2013 |

OTHER PUBLICATIONS

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.

Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.

Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.

McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.

Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.

Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.

Schnakenberg, U., et al, "Initial Investigations on Systems for Measuring Intraocular Pressure," Sensors and Actuators, 2000, p. 287-291, vol. 85, Elsevier Science B.V., Germany.

Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.

Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.

Van Schuylenbergh, K., et al, "All Implantable Telemetric Tonometer for Direct Intraocular Pressure Measurements," 1st European Conference on Biomedical Engineering, Feb. 1991, pp. 194-195, vol. 17, No. 20, Nice, France.

"Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine."

International Searching Authority, International Search Report, PCT/US2012/057426, Jan. 18, 2013, 6 pages.

International Searching Authority, Written Opinion of the International Searching Authority, PCT/US2012/057246, Jan. 18, 2013, 10 pages.

International Searching Authority, Search Report and Written Opinion of the International Searching Authority, PCT/US2010/033329, Jul. 13, 2010, 14 pages.

International Searching Authority, Search Report and Written Opinion of the International Searching Authority, PCT/US2010/047600, 13 pages.

International Searching Authority, Search Report and Written Opinion of the International Searching Authority, PCT/US2010/047429, 15 pages.

International Searching Authority, Search Report and Written Opinion of the International Searching Authority, PCT/US2010/049424, 15 pages.

* cited by examiner

SELECTABLE VARIED CONTROL VALVE SYSTEMS FOR IOP CONTROL SYSTEMS

BACKGROUND

The present disclosure relates generally to valves and associated systems and methods for use in ophthalmic treatments. In some instances, embodiments of the present disclosure are configured to be part of an IOP control system.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous drainage system. The delicate balance between the production and drainage of aqueous humor determines the eye's IOP.

Figure 1:
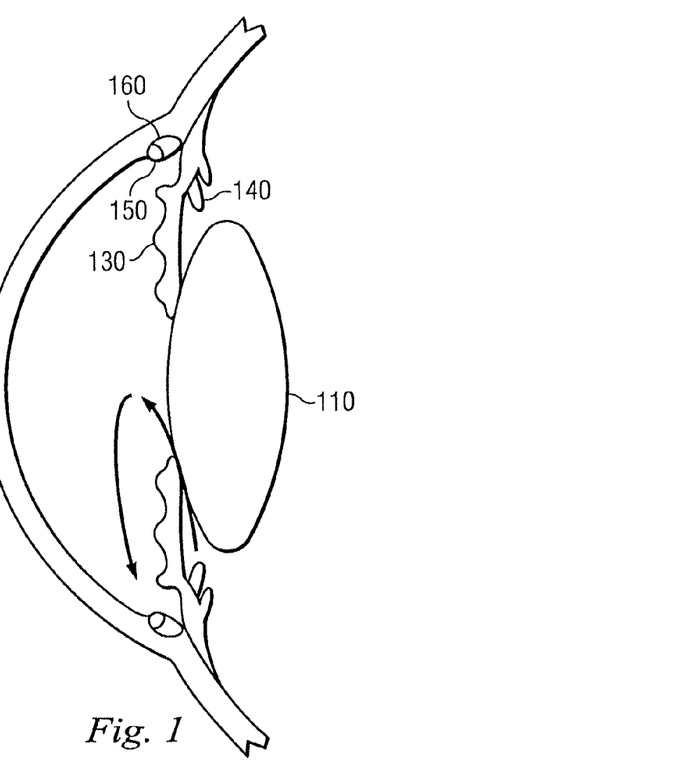
FIG. 1 is a diagram of the front portion of an eye.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering TOP. These devices are generally passive devices and do not provide a smart, interactive control of the amount of flow through the drainage tube. In addition, fluid filled blebs frequently develop at the drainage site. The development of the bleb typically includes fibrosis, which leads to increased flow resistance and it is generally the case that this resistance increases over time. This development and progression of fibrosis reduces or eliminates flow from the anterior chamber, eliminating the capacity of the drainage device to affect IOP.

The system and methods disclosed herein overcome one or more of the deficiencies of the prior art.

SUMMARY

In one exemplary aspect, the present disclosure is directed to a selectable IOP valve for implantation in an eye of a patient. The valve may comprise a flow control valve system configured to control flow rates of the aqueous. The valve system may comprise a plurality of flow control pathways arranged to operate in parallel with each other. Each of the flow control pathways may be in communication with an entry port to the valve system. A flow control mechanism is associated with each of the plurality of flow control pathways, and the flow control mechanism is arranged to selectively control aqueous flow rates through the passageways.

In one aspect, the flow control mechanism comprises a single flow control mechanism associated with multiple flow control pathways of the plurality of flow control pathways. In another aspect, the flow control mechanism comprises a separate flow control mechanism associated with each flow control pathway of the plurality of flow control pathways. In some aspects, each of the separate flow control mechanisms comprise a membrane valve.

In one aspect, the IOP valve comprises a first pressure sensor located in fluid communication with the anterior chamber of an eye and a second pressure sensor located in a drainage location. A difference between readings from the first pressure sensor and the second pressure sensor approximates a pressure differential between the anterior chamber and the drainage location. In another aspect, the IOP valve comprises a first pressure sensor located in a drainage location and a remote pressure sensor located remotely from the first pressure sensor such that the remote pressure sensors measures or approximates atmospheric pressure. A difference between readings from the first pressure sensor and the remote pressure sensor approximates pressure in the drainage location.

In another exemplary aspect, the present disclosure is directed to a method performed by an IOP control system that drains aqueous from an anterior chamber of the eye to a drainage location of the eye. The method may comprise detecting pressure within an anterior chamber of the eye, detecting pressure at a drainage location of the eye, and determining whether to adjust drainage aqueous flow based on the detected pressures by comparing the detected pressures in both the anterior chamber and the drainage location to pre-established acceptable pressures. Drainage aqueous flow from the anterior chamber is adjusted by adjusting access to one of a plurality of parallel flow paths to achieve pressures in both the anterior chamber and the drainage location corresponding to the acceptable pressures.

In another exemplary aspect, the present disclosure is directed to a selectable IOP valve for implantation in an eye of a patient. The valve may comprise a drainage pathway arranged to carry aqueous from an anterior chamber of an eye, a first flow control pathway in communication with the drainage pathway, and a second flow control pathway in communication with the drainage pathway; the first and second flow control pathways being arranged to carry aqueous in parallel from the drainage pathway.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and method disclosed herein and together with the description, serve to explain the principles of the present disclosure.

DETAILED DESCRIPTION OF THE PREFERRED EMBODIMENTS

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

In some particular instances, embodiments of the present disclosure are configured to be part of the glaucoma drainage devices disclosed in U.S. patent application Ser. No. 12/832,449, filed Jul. 8, 2010 and U.S. patent application Ser. No. 12/837,803, filed Jul. 16, 2010, which are a continuation-in-part applications of U.S. application Ser. No. 12/685,772 filed Jan. 12, 2010, which is a continuation-in-part of U.S. application Ser. No. 12/609,043 filed Oct. 30, 2009, which is a continuation-in-part of U.S. application Ser. No. 12/563,244 filed Sep. 21, 2009, each of which is hereby incorporated by reference in its entirety.

Figure 2:
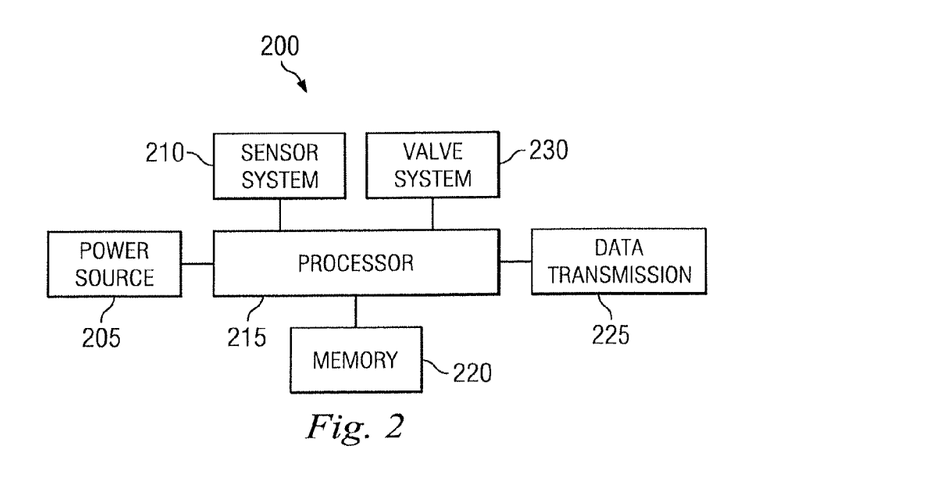
FIG. 2 is a block diagram of an exemplary IOP control system according to the principles of the present disclosure.

FIG. 2 is a block diagram of an exemplary IOP control system 200 implantable in an eye of a patient, such as the eye in FIG. 1, for the treatment of glaucoma or other conditions. The IOP control system 200 is configured in a manner that provides IOP pressure control, but also regulates and controls bleb pressures, reducing complications arising from surgical implant glaucoma treatments. In FIG. 2, the IOP control system 200 includes a power source 205, an IOP sensor system 210, a processor 215, a memory 220, a valve system 230, and a data transmission module 225.

The power source 205 is typically a rechargeable battery, such as a lithium ion or lithium polymer battery, although other types of batteries may be employed, both chargeable and non-chargeable types. In addition, any other type of power cell is appropriate for power source 205. Power source 205 provides power to the system 200, and more particularly to processor 215. In one example, the power source 205 can be recharged via an RFID link or other type of inductive coupling.

Processor 215 is typically an integrated circuit with power, input, and output pins capable of performing logic functions. In various embodiments, processor 215 is a targeted device controller. In such a case, processor 215 performs specific control functions targeted to a specific device or component, such as a data transmission module 225, power source 205, sensing system 210, valve system 230, or memory 220. In other embodiments, processor 215 is a microprocessor. In such a case, processor 215 is programmable so that it can function to control more than one component of the device. In other cases, processor 215 is not a programmable microprocessor, but instead is a special purpose controller configured to control different components that perform different functions.

Memory 220 is typically a semiconductor memory such as RAM, FRAM, or flash memory. Memory 220 interfaces with processor 215. As such, processor 215 can write to and read from memory 220. For example, processor 215 can be configured to read data from the IOP sensor system 210 and write that data to memory 220. In this manner, a series of IOP readings can be stored in memory 220. Processor 215 is also capable of performing other basic memory functions, such as erasing or overwriting memory 220, detecting when memory 220 is full, and other common functions associated with managing semiconductor memory.

Data transmission module 225 may employ any of a number of different types of data transmission. For example, data transmission module 225 may be an active device such as a radio. Data transmission module 225 may also be a passive device such as the antenna on an RFID tag. In this case, an RFID tag includes memory 220 and data transmission module 225 in the form of an antenna. An RFID reader can then be placed near the system 200 to write data to or read data from memory 220. Since the amount of data typically stored in memory 220 is likely to be small (consisting of IOP readings over a period of time), the speed with which data is transferred is not crucial. Other types of data that can be stored in memory 220 and transmitted by data transmission module 225 include, but are not limited to, power source data (e.g. low battery, battery defect), speaker data (warning tones, voices), IOP sensor data (IOP readings, problem conditions), time stamp data and the like.

Alternatively, data transmission module 225 may be activated to communicate an elevated IOP condition to a secondary device such as a PDA, cell phone, computer, wrist watch, custom device exclusively for this purpose, remote accessible data storage site (e.g. an internet server, email server, text message server), or other electronic device. In one embodiment, a personal electronic device uploads the data to the remote accessible data storage site (e.g. an internet server, email server, text message server). Information may be uploaded to a remote accessible data storage site so that it can be viewed in real time, for example, by medical personnel. For example, in a hospital setting, after a patient has undergone glaucoma surgery and had system 200 implanted, a secondary device may be located next to the patient's hospital bed. Since IOP fluctuations are common after glaucoma surgery (both on the high side and on the low side which is also a dangerous condition), processor 215 can read IOP measurements made by an implanted IOP sensor system 210. If processor 215 reads an unsafe IOP condition, data transmission module 225 can alert the patient and medical staff directly or by transmitting the unsafe readings to a secondary device.

Figure 3:
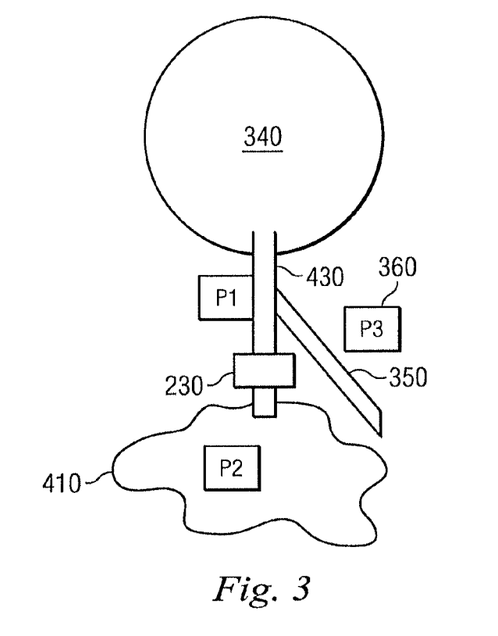
FIG. 3 is a diagram of an exemplary IOP control system according to the principles of the present disclosure.

FIG. 3 is a diagram of the exemplary IOP sensor system 210, the drainage tube 430, valve system 230, and divider 350. In FIG. 3, the exemplary IOP sensor system 210 includes three pressure sensors, P1, P2, and P3. Pressure sensor P1 is located in or is in fluidic communication with the anterior chamber 340, the pressure sensor P2 is located at a drainage site in the subconjunctival space and is arranged to measure bleb pressure, and pressure sensor P3 is located remotely from P1 and P2 in manner to measure atmospheric pressure. In some embodiments, pressure sensor P1 is located in a lumen or tube that is in fluid communication with the anterior chamber.

The drainage tube 430 drains aqueous from the anterior chamber 340 of the eye. The valve system 230 controls the flow of aqueous through the drainage tube 430. In the embodiment shown, the pressure sensor P1 measures the pressure in the tube 430 upstream from the valve system 230 and downstream from the anterior chamber 340. In this manner, pressure sensor P1 measures the pressure in the anterior chamber 340. The expected measurement discrepancy between the true anterior chamber pressure and that measured by P1 when located in a tube downstream of the anterior chamber (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

In some embodiments, the divider 350 separates pressure sensor P2 from pressure sensor P3. Pressure sensor P2 is located at a drainage site (e.g. 410 in FIG. 4). As such, pressure sensor P2 may be located in a pocket, such as a bleb, that generally contains aqueous or in communication with such a pocket, via a tube for example and is in a wet location 410. Pressure sensor P3 is physically separated from pressure sensor P2 by divider 350. Divider 350 is a physical structure that separates the wet location 410 of P2 from the relatively dry (and mechanically unstressed) location 360 of P3. In some embodiments, divider 350 is included when the system of the present invention is located on a single substrate, such as from fabrication on a Silicon wafer or other suitable planar substrate. In this configuration, all three pressure sensors (P1, P2, and P3) are located on a substrate that includes tube 430, valve system 230, divider 350, and the other components of the system. Note that the divider 350 may take many forms, such as but not limited to a tube that couples pressure sensor P3 fluidically with a site away from the substrate, or as a pocket residing on the top portion of the substrate away from and fluidically independent of the drainage site.

In some embodiments of the present invention, the atmospheric pressure sensor P3 is located in close proximity to the eye, and in one embodiment, the pressure sensor P3 may be implanted in the eye under the conjunctiva. In such a case, pressure sensor P3 measures a pressure that can be correlated with atmospheric pressure. For example, true atmospheric pressure can be a function of the pressure reading of pressure sensor P3. Pressure sensor P3 may also be located in a dry portion 360 of the subconjunctival space, separate from the drainage location. Regardless of location, pressure sensor P3 is intended to measure atmospheric pressure in the vicinity of the eye or at the eye's surface. One embodiment of the location of P3 is that if the system has the standard GDD plate style shape, then P3 may reside on the top with a barrier preventing it from being crushed while still allowing pressure communication through the conjunctiva, while P2 resides on the bottom in direct contact with the drainage site.

In a different embodiment, P3 is not located on the implant but is located outside of the eye as part of a separate external component or subsystem such as a wearable element (e.g. glasses, hat, headband, armband, bracelet, necklace or belt) or a device that resides in proximity to the patient (e.g. a pillow, nightstand). Such as subsystem, which may or may not include sensor P3, may include an external recharging implant that is at least temporarily placed near the implant location in order to recharge the implant power source 205 and or download data from memory 220 via the data transmission module 225.

Generally, IOP is a gauge pressure reading—the difference between the absolute pressure in the eye (as measured by P1) and atmospheric pressure (as measured by P3). Atmospheric pressure, typically about 760 mm Hg, often varies in magnitude by 10 mmHg or more depending on weather conditions or indoor climate control systems. In addition, the effective atmospheric pressure can vary significantly and in some cases rapidly—with changes in excess of 100 mmHg—if a patient goes swimming, hiking, diving, riding in an airplane, etc. Such a variation in atmospheric pressure is significant since IOP is typically in the range of about 15 mm Hg. Thus, for accurate monitoring of IOP, it is desirable to have pressure readings for the anterior chamber (as measured by P1) and atmospheric pressure in the vicinity of the eye (as measured by sensor P3).

Therefore, in one embodiment of the present invention, pressure readings are taken by P1 and P3 simultaneously or nearly simultaneously over time so that the actual IOP can be calculated (as P1-P3 or P1-$f$(P3), where f(P3) indicates a function of P3). The pressure readings of P1 and P3 can be stored in memory 220 by processor 215. They can later be read from memory so that actual IOP over time can be interpreted by a physician.

Pressure sensors P1, P2, and P3 can be any type of pressure sensors suitable for implantation in the eye. They each may be the same type of pressure sensor, or they may be different types of pressure sensors. For example, pressure sensors P1 and P2 may be the same type of pressure sensor (implanted in the eye), and pressure sensor P3 may be a different type of pressure sensor (in the vicinity of the eye).

Figure 4:
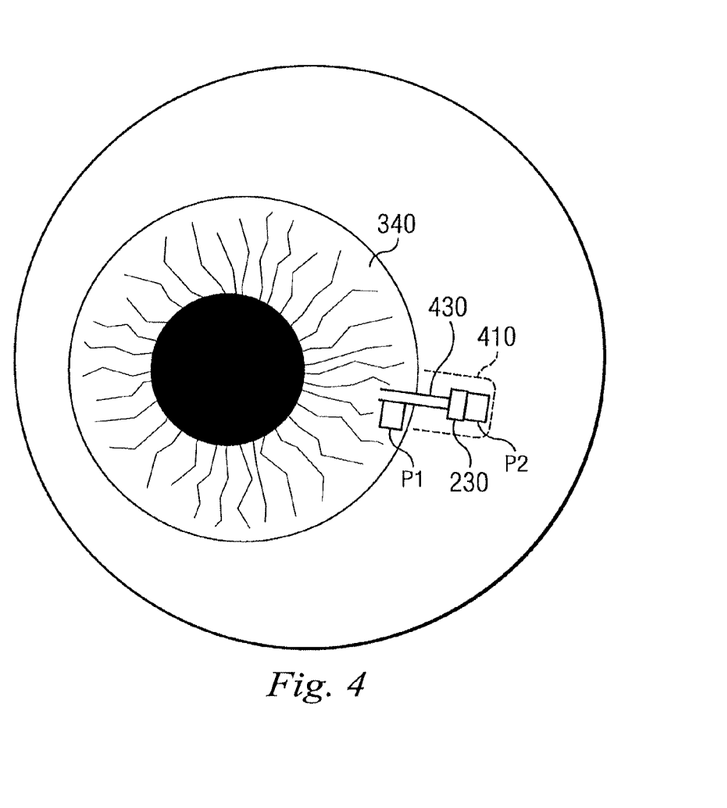
FIG. 4 is a diagram of one possible application of the IOP sensor system of the present disclosure.

In another embodiment of the present invention, pressure readings taken by pressure sensors P1 and P2 can be used to control a device that drains aqueous from the anterior chamber 340. FIG. 4 is a diagram of one possible application of the sensors in a system utilizing the readings of pressures sensors P1-P3. In FIG. 4, pressure sensor P1 measures the pressure in the anterior chamber 340 of the eye. Pressure sensor P2 measures the pressure at a drainage site 410.

The drainage tube 430 may be arranged to shunt fluid from the anterior chamber 340 to the drainage location 410, which may be at any of numerous locations within the eye. For example, some tubes are arranged to shunt aqueous from the anterior chamber 340 to the subconjunctival space thus forming a bleb under the conjunctiva or alternatively, to the subscleral space thus forming a bleb under the sclera. Other tube designs shunt aqueous from the anterior chamber to the suprachoroidal space, the supraciliary space, the juxta-uveal space, or to the choroid, forming blebs in those respective locations. In other applications, the drainage tube shunts aqueous from the anterior chamber to Schlemm's canal, a collector channel in Schlemm's canal, or any of a number of different blood vessels like an episcleral vein. In some examples, the drainage tube even shunts aqueous from the anterior chamber to outside the conjunctiva. Each of these different anatomical locations to which aqueous is shunted is an example of a drainage location 410. Other examples of a drainage location 410 include, but are not limited to: a subconjunctival space, a suprachoroidal space, a subscleral space, a supraciliary space, Schlemm's canal, a collector channel, an episcleral vein, and a uveo-scleral pathway.

In FIG. 4, the tube 430 with the valve system 230 on one end is located with one end in the anterior chamber 340 and the other end in the drainage location 410, with P1 located within the anterior chamber 340. The valve system 230 controls the flow of aqueous from the anterior chamber 340 to the drainage location 410. As indicated above, the pressure sensor P1 is located in the anterior chamber (as illustrated in FIG. 4) or located in the subconjuctival space in fluid communication with the anterior chamber 340 (as illustrated in FIG. 3), in either version pressure sensor P1 is located upstream from valve system 230.

Since pressure sensor P1 measures the pressure in the anterior chamber 340 and pressure sensor P2 measures pressure at the drainage location 410, the difference between the readings taken by these two pressure sensors (P1-P2) provides an indication of the pressure differential between the anterior chamber 340 and the drainage location 410. In one embodiment, this pressure differential is an important factor in dictating the rate of aqueous flow from the anterior chamber 340 to the drainage location 410.

One complication involved with surgery that shunts the anterior chamber 340 to a drainage location 410 is hypotony—a dangerous drop in IOP that can result in severe consequences. It is desirable to control the rate of aqueous outflow from the anterior chamber 340 to the drainage location 410 so as to prevent hypotony. Readings from pressure sensors P1, P2, and P3 can be used to control the flow rate through tube 430 by controlling the valve system 230. For example, the valve system 230 can be controlled based on the pressure readings from pressure sensors P1, P2, and P3.

In another embodiment of the present invention, IOP (based on readings from pressure sensor P1 and pressure sensor P3) can be controlled by controlling valve system 230. In this manner, IOP is the control parameter. To accomplish this, the valve system 230 can be adjusted to maintain a particular IOP (like an IOP of 15 mm Hg). Valve system 230 may be opened more at night than during the day to maintain a particular IOP. In other embodiments, an IOP drop can be controlled. Immediately after surgery, IOP can drop precipitously. Valve system 230 can be adjusted to permit a gradual drop in IOP based on readings from pressure sensors P1 and P3. In one such example, the physician would be able to set and occasionally update the high/low IOP thresholds wirelessly to meet each patient's specific requirements.

In another embodiment of the present invention, readings from pressure sensor P2 (or from the difference between pressure sensor P2 and atmospheric pressure as measured by P3) can be used to control valve system 230 so as to control the morphology of a bleb. One of the problems associated with implant surgery is bleb failure. A bleb can fail due to poor formation or fibrosis. The pressure in the bleb is one factor that determines bleb morphology. As explained above, too much pressure can cause a bleb to migrate to an undesirable location or can lead to fibrosis. The pressure of the bleb can be controlled by using the reading from pressure sensor P2 (at drainage location 410—in this case, a bleb). In one embodiment of the present invention, the difference between the pressure in the bleb (as measured by P2) and atmospheric pressure (as measured by P3) can be used to control valve system 230 to maintain a desired bleb pressure. In this manner, the pressure sensors used to determine IOP as defined in the present invention can also be used to control fluid flow in order to properly maintain a bleb.

Valve system 230 may be controlled by microprocessor 215 based on input data received from the sensors. A desired pressure differential (that corresponds to a desired flow rate) can be maintained by controlling the operation of valve system 230. Likewise, a desired IOP, IOP change rate, or bleb pressure can be controlled by controlling the operation of valve system 230. Furthermore, flow across the valve may drastically vary with time.

Figure 5:
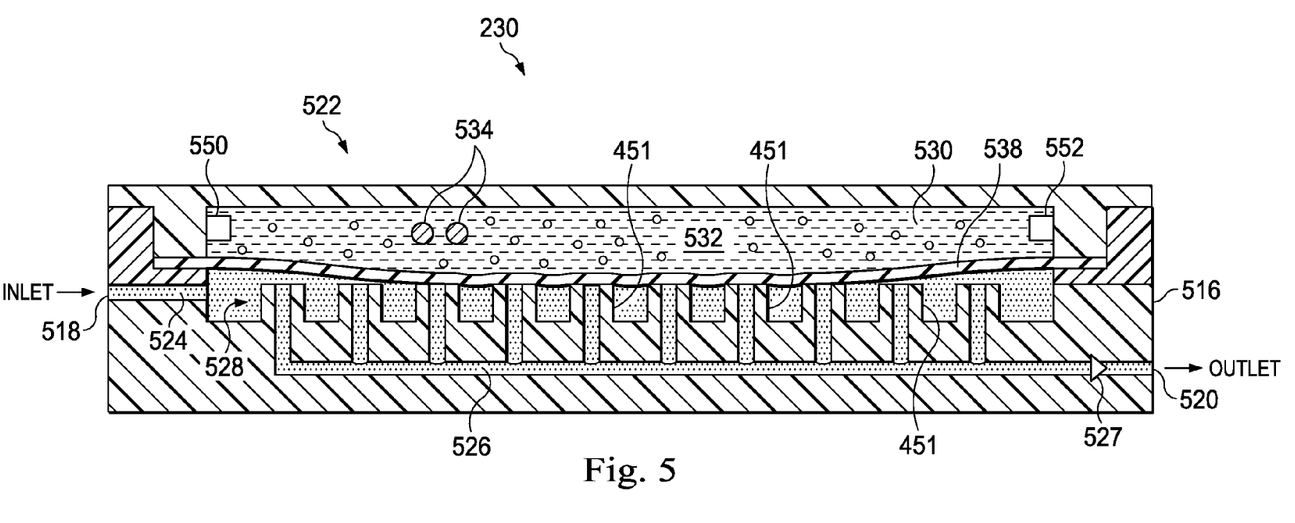
FIG. 5 is an illustration of a cross-sectional view of an exemplary valve system according to one embodiment consistent with the principles of the present disclosure.

FIG. 5 shows an exemplary embodiment of the valve system 230 in greater detail. The valve system 230 is disposed along, and may form a part of, the drainage tube 430 between the tube end in the anterior chamber and the drainage site.

The valve system 230 is configured to control the flow of drainage fluid through the drainage line, and thereby control pressure in the eye, including the IOP. For example, when IOP is high, the valve system 230 may operate to permit increased flow through the drainage tube, and when IOP is low, the valve system 230 may operate to decrease the flow through the drainage tube. The valve system 230 is configured to monitor pressure and controls drainage fluid flow to the bleb. This may decrease fibrosis and increase absorption efficiency. To accomplish this, the valve system 230 is responsive to signals sent as instructions from the processor 215. Processor 215 instructions to the valve system 230 are a function of the pressure measurements taken by the pressure sensors P1, P2, and P3, and/or the IOP as determined by detected pressures and may also be a function of the time, the number of days since implantation or some other variable.

In the example in FIG. 5, the valve system 230 includes a housing 516 with an entrance port 518 and an exit port 520, a flow control system 522 in the housing 516, an inlet passageway 524, an outlet passageway 526, and a nozzle array 528 extending between the inlet and outlet passageways 524, 526. The entrance port 518 connects to the drainage tube 430 and is configured to receive aqueous flowing from the drainage tube 430. The exit port 520 permits aqueous to exit the housing 516 for release at the drainage site 410 or for further regulation. The entrance port 518 connects to the drainage tube and the exit port 520 leads to the drainage site. In this example, a check valve 527 is associated with the housing 516 to reduce the likelihood of backflow.

The flow control system 522 includes a flow control chamber 530, an actuator fluid 532 in the flow control chamber 530, electrodes 534 arranged to cooperate with the actuator fluid 532, and a flexible membrane 538. In operation the electrodes 534 generate bubbles in the actuator fluid 532 through electrolysis, increasing the pressure within the chamber of the flow control chamber 530. As the pressure increases, the flexible membrane 538 expands into the inlet passageway 524, increasing the volume within the flow control chamber and decreasing the cross-sectional area of the inlet passageway 524, thereby restricting some aqueous flow from the drainage tube 430 by occluding a portion or all of the nozzle array 528. In a similar, but opposite manner, as the solution in the flow control chamber 530 returns to a state of more liquid (less gas), the volume and pressure in the chamber 530 decreases, permitting the flexible membrane 538 to move further out of the inlet passageway 524, thereby permitting an increased level of aqueous flow (per mmHg of differential pressure along the fluid flow path) from the drainage tube 430 through the inlet passageway 524.

As can be seen in FIG. 5, in the example shown, the flow control chamber is formed in the housing 516 with rigid structure formed by the housing walls on three sides. The chamber 530 is sealed closed by the flexible membrane 538. Accordingly, as volume increases, the pressure increase acts to displace the membrane 538 in only one direction.

The flexible membrane 538 may be formed of an elastically deformable elastomeric material or other materials of adequate flexibility at the relevant dimensions including without limitation, materials such as a silicon, silicon nitride (including stoichiometric or low-stress nitrides), silicone elastomeric rubber, polyimide, Parylene, Kapton, polypropylene, polyethylene, metals, composite materials, and others. In the example shown, the flexible membrane 538 is secured to the housing 516 at its edges. Although shown in cross section, the flow control chamber 530 may be disposed to form a circular or cylindrical chamber, with the flexible membrane 538 being secured along the diameter. Accordingly, the flexible membrane 538 may be a circular material secured at its periphery to the housing 516. As such, as the volume or pressure increases within the chamber, the central portion of the flexible membrane undergoes the highest level of displacement. In other embodiments, the housing and flexible membrane is formed so that the membrane has a non-circular shape, including oval, substantially rectangular, or square, for example. Other shapes are also contemplated. Applicable to all flexible membranes such as 538 may also have corrugation features (such as ridges and valleys), and the specific feature dimensions will affect the displacement response.

The actuator fluid 532 is contained in the flow control chamber 530 and, in some embodiments, includes water. Some embodiments include a saline like sodium chloride in the water.

The electrodes 534 are disposed within the actuator fluid 532 in a manner permitting at least one or more components of the actuator fluid 532 to phase change from liquid to gas, forming the bubbles through electrolysis. As this occurs, the pressure in the chamber increases, thereby increasing overall pressure. This increased pressure acts on the flexible membrane 538 to cause its displacement. The electrodes are in electrical communication with the power source 205, which is controlled by the processor 215. Through the electrolysis, some portion of the water in the actuator fluid 532 may be converted to gaseous hydrogen and oxygen molecules. Although only two adjacent electrodes are shown, these are representative of a number of electrodes, including interdigitated electrodes that may be used. In one exemplary embodiment shown the electrodes 534 are interdigitated for efficient and effective electrolysis, for example in terms of response speed and required voltage.

In alternative embodiments, the flow control system 522 includes a mechanical displacement system 550 that mechanically displaces the flexible membrane to regulate aqueous flow through the valve system. In one example, the mechanical displacement system 550 is a gear and rack system where displacement includes driving the gear. Other mechanical displacement systems are also contemplated. Such actuation mechanisms can include any practical means for mechanical or electromechanical actuation, such as electromagnetic, electrokinetic, electrostatic, non-electrochemical phase change (such as thermal), thermal bimorph, shape memory alloy, piezoelectric, and the like.

Some embodiments of the valve system 230 include a latch 552 that enables the flexible membrane 538 to be secured and maintained in its displaced condition. The use of such a latch 552 enables the flow through the valve system 230 to be modified, but then enables the position of the membrane to be maintained over time without the need for constant or intermittent power-consuming adjustments to maintain the volume or pressure in the flow control chamber 530. In some examples, the latch 552 is a mechanical hook latch that captures the membrane and holds it in place until it is desired to be released. Accordingly, the latch 552 may secure the flexible membrane in a position so that the passageway is substantially closed, substantially open, or at any desired position. This mechanical hook latch may be controlled and operated by the processor. In other examples, the latch 552 is a mechanical displacement controlling the position of the edge of the membrane to move it relative to the passageway. Some embodiments use resistance or non-resistance latches. Some may require energy to disengage, but require no energy to engage. Some latches are biased with a spring constant biasing member.

In the example shown, the nozzle array 528 is made up of a plurality of individual nozzle passageways (flow channels) formed in parallel to each extend through a boss 451 that projects into the inlet passageway 524. As will be further described below, the bosses 451 are arranged to cooperate with the flow control system 522 to control aqueous flow through the valve system 230. In accordance with this, the nozzle passageways of the nozzle array 528 are substantially perpendicular to the general plane of the flexible membrane 538, and the upper surface of the bosses 451 are arranged to be substantially parallel to the general plane of the flexible membrane 538. Because of this arrangement, the flexible membrane 538 in this exemplary embodiment can provide, for a given slight movement of 538, a more gradual change in flow by designing the array appropriately. This occurs because the flexible membrane 538 may act in some respects as a cap on one or more passageways of the array of nozzle passageways. In some aspects, the flexible membrane 538 is arranged to cover the entire upper surface of one or more of the bosses 451, and may even stretch to extend at least partially along the sides of individual bosses 451 adjacent to the edge between the top of the boss 451 and the sides.

As can be seen, the single flexible membrane 538 controls access to the plurality of nozzle passageways. Due to the elastic nature of the flexible membrane, the greatest degree of deflection is at the center and as a result the nozzles in the center area of the nozzle array 528 are blocked by the flexible membrane, while the nozzles at the outer edges have greater spacing. This results in higher flow rates at the edges of the array than the center of the array when the flexible membrane is initially displaced. As the displacement of the membrane increase the area of blocked nozzle passageways increases and thus the flow rate decreases. It should also be understood that, for the fully open configuration (maximum flow), the plurality of nozzles forces a more uniform distribution of flow across the valve in comparison to a valve in which the outlet is a single exit port with an exit area approximately equivalent to the sum of the proposed nozzle array. Secondly, the (possibly quite large) spacing of the nozzles ensures that a reduction in sensitivity of flow rate to the membrane motion can be realized; that is, as this spacing is increased, the sensitivity will decrease. These last two points support the utilization of the nozzle array to increase control (granularity). In some embodiments, the nozzle array 528 comprises approximately consistent pathway widths for all nozzles; in other embodiments, such width is varied from nozzle to nozzle.

The systems and methods described herein achieve IOP control with very low power and with a very small device. The system takes into account bleb pressure in regulating drainage flow. Accordingly, based on pressure sensor inputs and periodic power boosts to control the flow-regulating control valves, the system provides suitable eye care for a patient. In some examples, sufficient power is provided through on-board batteries or unobtrusive wireless (external) powering.

In some exemplary embodiments, the processor 215 is configured to calculate flow rates, and thus determine whether to change the valve pressure in view of detected pressures, based on the orifice size, channel resistance, and other system resistances within the valve system 230. As such, based on the designed dimensions of the valve, the system can determine flow for particular detected pressures. Here, the processor 215 is configured to calculate or determine the flow rate when there are multiple identical flow paths, as is the case in the valve system 230, with its nozzle array 528. For example, when only part of the array 528 is open with n through-pathways, the overall flow resistance will be affected by the part of the array 528 that is accessible (a combination of the through-hole resistance/n and the membrane-controlled channel height that leads to the array).

$$\text{Flow Rate}_1 = \Delta P_1/(\text{Orifice resistance}/n_1 + \text{channel resistance} + \text{other system resistances})$$

Here, the channel resistance is the volume in which the membrane moves (space downstream of the inlet passageway 524, but upstream of the actual array of passages 528). The "system resistances" includes resistance from the entrance port 518, inlet passageway 524, outlet passageway 526, and the exit port 520. Note that the "orifice resistance" is the sum of the resistances associated specifically with the array of passages 528.

When the membrane is deflected further so that access to more through-holes is granted, the new flow rate becomes:

$$\text{Flow rate}_2 = \Delta P_2/(\text{Orifice resistance}/n_2 + \text{channel resistance} + \text{other system resistances})$$

Note that the value of the channel resistance changes with membrane deflection, but if the channel and other system resistances are low enough compared to the value of orifice resistance/n, the flow control can roughly approach linearity:

$$\text{Flow rate}_2/\text{flow rate}_1 \alpha \Delta P_2 n_2/\Delta P_1 n_1$$

Therefore, if the number of exposed nozzles, n, is linearly controllable (or at least more so in comparison to the single exit nozzle case), then the flow rate is approximately linearly controllable (see comment above regarding nozzle spacing).

Figure 6:
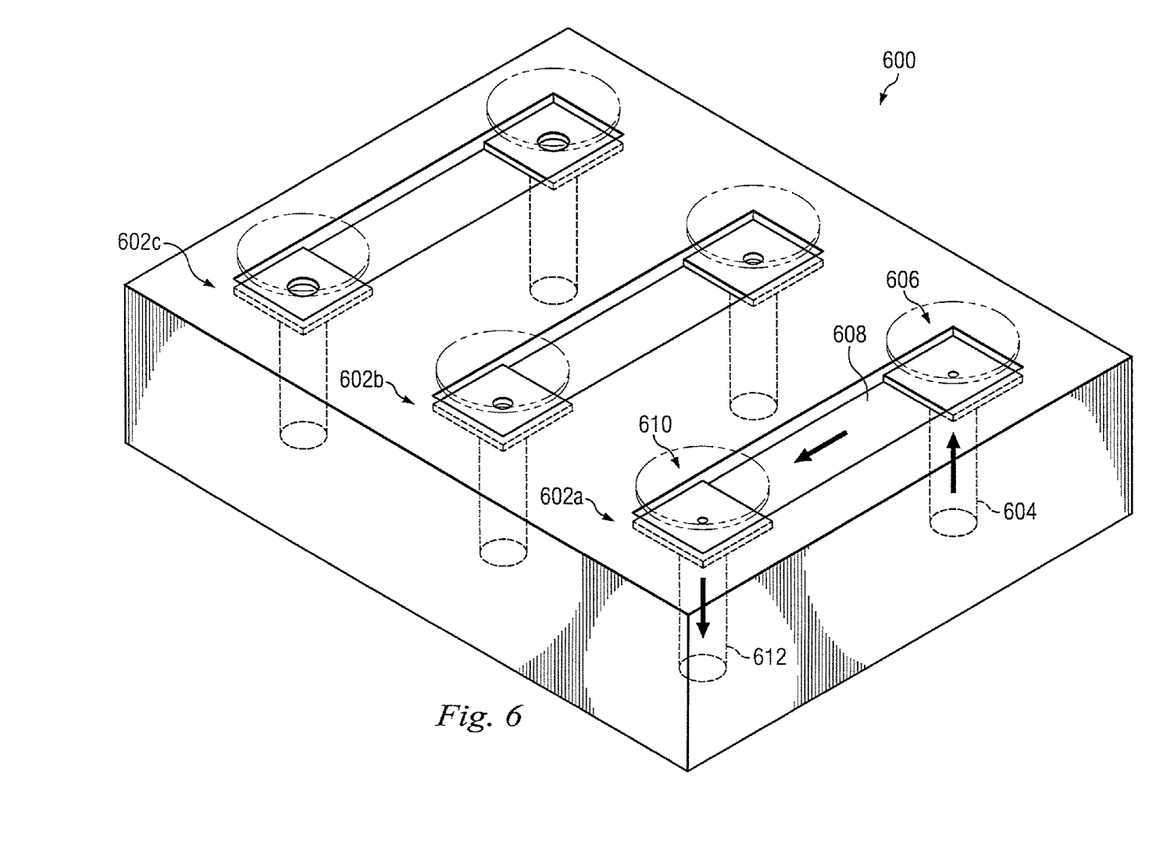
FIG. 6 is an illustration of a plan view of an exemplary valve system according to another embodiment consistent with the principles of the present disclosure.
Figure 7:
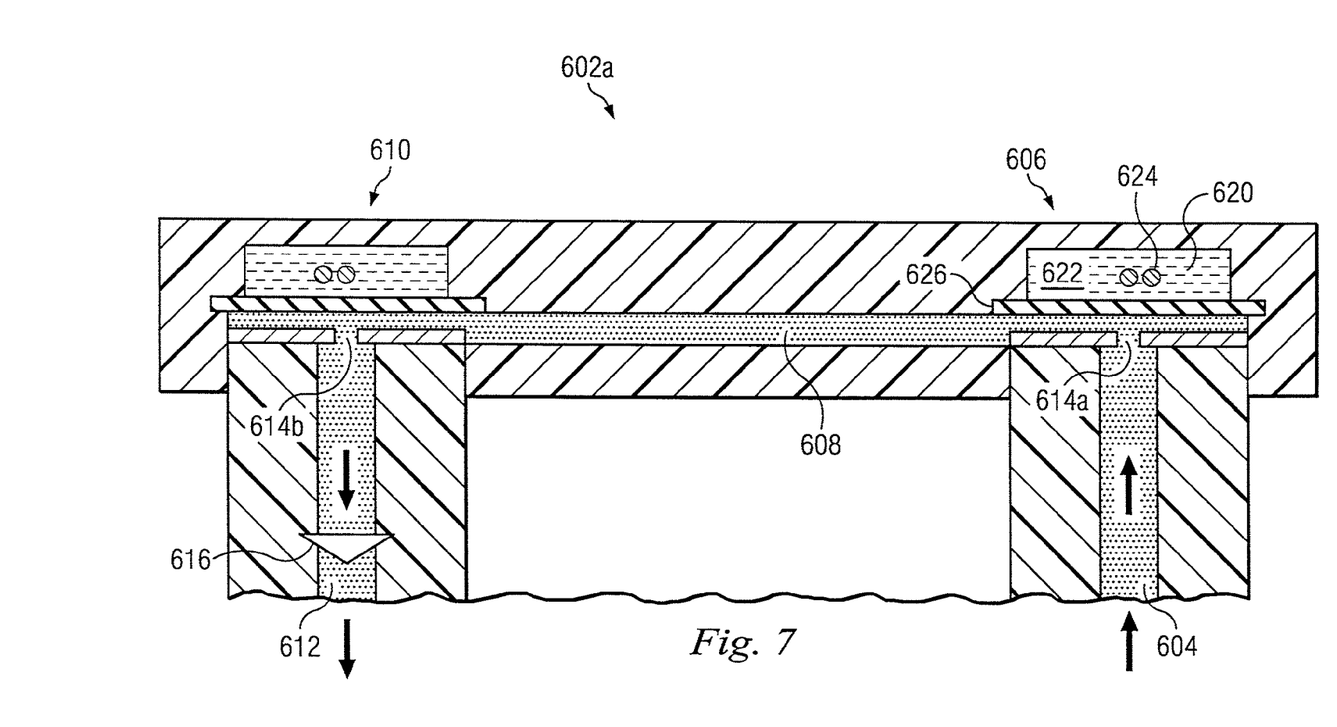
FIG. 7 is an illustration of a cross-sectional view of an exemplary valve system according to the embodiment shown in FIG. 6.

FIGS. 6 and 7 show yet another embodiment of a valve system 230. This valve system is referred to herein by the reference numeral 600. The valve system 600 includes a plurality of flow paths 602a-c arranged in parallel. The flow paths 602a-c are arranged to operate in parallel and receive aqueous from an entry point to the valve system. Only three flow paths are shown for convenience, but more or less than three flow paths may be employed. Each of the plurality of flow paths 602a-c is arranged to permit aqueous flow at a different flow rate to regulate to different IOP levels. That is, individual paths have a varied resistance to flow so that the flow path 206a has a different resistance than the flow path 206b and so on.

FIG. 7 shows the exemplary flow path 602a in cross-section. It is understood that the flow paths 602b and 602c may be similarly arranged. Referring to FIG. 7, the flow path 602a includes an inlet passage 604 that may connect to the drainage tube 430 in FIG. 3, a first flow control system 606, an intermediate pathway 608, a second flow control system 610, and an outlet passage 612 exiting from the valve system 600. The outlet passage 612 may exit to a common outlet line (not shown), which may drain to the drainage site 410 in FIGS. 3 and 4. In this example, a check valve 616 is associated with the housing outlet passage 612 to reduce the likelihood of backflow. Although shown in the outlet passage 612, the checkvalve 616 may be disposed at any location along the flow line.

As shown in FIG. 7, the inlet and outlet passages include respective orifices 614a, 614b adjacent the flow control systems 606, 610. For each of the different flow paths 602a-c, these orifices 614a, 614b are sized to create a particular orifice resistance to achieve different flow rates. For example, in the embodiments shown, the flow path 602b may include orifices sized relatively larger than the orifices in flow path 602a. Thus, the flow path 602b may permit a higher aqueous flow rate than the path 602a. And the orifices in flow path 602c may include orifices sized relatively larger than the orifices in flow path 602b. Thus, the flow path 602c may permit a higher aqueous flow rate than the path 602a.

In the example shown, the three channels 602a-c are intended to illustrate the low-volume, medium volume, and high volume flow rates can be accommodated as needed in response to the differential pressure encountered. This allows the flow response to be tuned around a few distinct set points of interest.

With reference to FIG. 7, access to the flow paths 602a-c is open, partially blocked, or completely blocked by the flow control systems 606, 610. (Although a major advantage of the current invention is that discrete resistance settings can be realized with valves needed to only operate in the fully-open or fully-closed positions, in another embodiment additional control may be realized by operated valves in partially-blocked configurations.) Similar to the flow control system 522 described above, the flow control systems 606, 610 may include a flow control chamber 620, an actuator fluid 622 in the flow control chamber 620, electrodes 624 arranged to cooperate with the actuator fluid 622, and a flexible membrane 626. Flow through the orifice 614a may be affected by the position of the flexible membrane 626 relative to the orifices. The discussion above relating to membrane displacement is also applicable to the valve system 600, including the discussion relating to latches or other means for maintaining the valve at a particular flow setting. Further, while only the flow control system 606 is labeled, it is understood that the flow control system 610 may operate in the same manner. In an exemplary embodiment, a check valve is located in the flow path to prevent back flow from the drainage location 410 back into the anterior chamber 340. This valve may be in a multitude of locations such as adjacent to orifice 614a, orifice 614b, inlet 604, outlet 612, or any other location directly in the line of flow for the system.

Where the system has multiple parallel pathways, the processor 215 may determine the flow rates, and thus determine whether to modify the flow, based on the flow and the pressures as determined by the pressure sensor system 210. For example, the system may control the valve to provide different flow resistances depending on flow characteristics needed, such as a pre-set flow resistance depending on the healing state or condition of the patient (need high resistance, or low resistance, etc.) or where a particular setpoint might be needed for other reasons (like growing blockage downstream, requiring lower pressure drop upstream).

In one embodiment, the flow is calculated by the processor 215 based on pressure readings from two pressure sensors in the system that are separated by a known, fixed resistance, such as a rigid flow channel. In another embodiment, the implanted system includes a flow sensor. As indicated above, in some exemplary embodiments, the processor 215 is configured to calculate flow rates, and thus determine whether to change the valve pressure in view of detected pressures, based on the orifice size, channel resistance, and other system resistances within the valve system 230. Here, the processor 215 is configured to calculate or determine the flow rate when there are multiple flow paths with different flow resistances, as is the case in the valve system 600, with its structured flow paths, taking into account the contributions of the flow resistances in the channels and through-holes as well as in the variable membrane-influenced channels of the system.

In some examples, the processor may determine the level of flow using equations as set forth below. Particularly, since the valve system 600 comprises multiple flow pathways of different flow resistances (i.e., parallel arrangement), when only part of the array is open with n through-pathways for each of the different flow pathways, similarly to the approach above, the equations governing flow become (for two different flow resistances):

Flow rate$_1$=$\Delta P_1$/((Flow res$_a$+valve res$_a$)/$n_{1a}$)+((Flow res$_b$+valve res$_b$)/$n_{1b}$)+system res.)

Flow rate$_2$=$\Delta P_2$/((Flow res$_a$+valve res$_a$)/$n_{2a}$)+((Flow res$_b$+valve res$_b$)/$n_{2b}$)+system res.)

If the valve and other system resistances are low compared to the (flow pathway resistance/n) the flow control becomes more linear:

Flow rate$_2$/Flow rate$_1$$\alpha\Delta P_2$/$\Delta P$*(Flow res$_a$/$n_{1a}$+Flow res$_b$/$n_{1b}$)/(Flow res$_a$)/$n_{2a}$)+((Flow res$_b$)/$n_{2b}$)

Therefore, if the number of exposed nozzles, n, is linearly controllable (or at least more so in comparison to the single exit nozzle case), then the flow rate is linearly controllable (see comment above regarding nozzle spacing).

This approach yields greater control flexibility than the uniform array approach with the cost of a slightly higher complexity. These approaches to obtain a more linear flow response may be useful as part of the system designs if the inherent nonlinearity of flow vs. channel height becomes problematic for the control system. In other embodiments, a non-linear (steeper or softer) response may be design goal.

In one alternative exemplary embodiment, the flow control systems 606, 610 are pressure-driven valves disposed in the aqueous paths to permit or restrict flow through the flow paths 602a-c wherein the pressures are those natural present in the eye (e.g. anterior chamber (P1), drainage location (P2), atmospheric pressure (P3)). Such systems may conserve additional power because the flow state may be maintained without additional energy. For flow control system 606, the position of flexible membrane 626 can be controlled by the pressure difference between flow control chamber 620 and pathway 604, wherein these volumes are in direct fluidic communication with either P1, P2, or P3 or other system pressures. For example, flow control chamber 620 may be in direct communication with P3 and pathway 604 in communication with P1; therefore, the IOP (P1-P3) determines the displacement of flexible membrane 626. In possibly the same embodiment, flow control system 610 can be controlled by the difference of P2-P3 (the bleb pressure level). Another embodiment could include any combination of the previously described electrolysis driven-valves and the pressure-driven valves. As described above, the latching and other features may also be used to maintain a particular flow setting without the use of power.

In some examples, each aqueous path 602a-c includes only one flow control system. While the second flow control system provides redundancy, a single flow control system in a single aqueous path 602a-c is also sufficient for controlling flow through the valve system 600. Consistent with this, some examples have only one flow control orifice, such as orifice 614a.

In use, the flow control systems 606, 610 are used to permit aqueous flow through the respective flow paths. Because each of the three flow paths shown in FIG. 6 permit aqueous flow at different flow rates, the desired flow rate may be achieved by mixing and matching the open and closed flow control systems to achieve the desired flow rate. For example, if flow path 602a permitted a flow rate of 15 units, path 602b permitted a flow rate of 10 units, and path 602c permitted a flow rate of 7 units, the processor may control the valve system 600 to provide flow rates of 7 units, 10 units, 15 units, 17 units, 22 units, 25 units, and 32 units, based on the settings of the flow control systems. Additional flow paths would provide additional flow rate options. Treatments plans also may be based on such control systems. For example, a treatment plan may include opening one aqueous pathway for a period of time after surgery, such as the first month after surgery, and later opening a second aqueous pathway to accomplish a desired flow, such as during the period of 2-6 months after surgery.

Because the system is arranged to take into account the bleb pressures, and output an optimum desired flow rate, the system may provide increased control of the drainage flow rate from the eye.

In use, the IOP control system modifies the fluid flow rates of aqueous to the drainage site. In one embodiment, the method begins with the sensors P1-P3 detecting pressures and the processor 215 receiving the data from the sensors.

Based upon algorithms, programs, or coding in the processor or memory, the processor 215 determines whether any flow modifications are required to maintain the IOP or the anterior chamber pressure within a desired target range and whether any modification is required to maintain the bleb pressure within a target range. In some aspects, the processor 215 compares measured pressure data to stored pressure data and determines whether the data is inside or outside acceptable ranges.

For example, in some aspects, determining whether flow modifications are required may include comparing the anterior chamber pressure as measured by sensor P1 to the atmospheric pressure as measured by sensor P3, and determining whether the valve system 230 should be modified based on the comparison. Other examples include other pressure relationships as determined by algorithms to control the valve system 230. Although several arrangements are contemplated, in one embodiment, the pressure measurements are weighted in the algorithms or calculation performed by the processor 215 so that the IOP will be decreased if necessary, at the expense of the bleb pressure.

If the system determines flow modifications are needed, the processor modifies the flow rates. In some examples disclosed herein, the valve system is a bubble operated device that modifies flow rates using pressure changes resulting from phase changes occurring during electrolysis procedures as discussed above. The pressure changes modify flow rates by opening and closing parallel flow paths. In other examples disclosed herein, the valve system is a pressure-driven device that modifies flow rates by opening and closing parallel flow paths, where each path is structurally configured to provide a different rate, to adjust the flow through the valve system, and does not necessarily require pressure sensors in order to operate Conventional passive check valves in drainage device implants (e.g. Ahmed Valve) only support reduced risk of hypotony in the weeks immediately following surgery. But these conventional valves have no mechanism for controlling bleb pressure. The systems disclosed herein can monitor bleb pressure and may adjust to control flow to the bleb. Accordingly, the systems and methods disclosed herein provide a device that a) requires minimal power (internal or external), and b) presents a mechanism of minimizing bleb height (reducing or eliminating bleb) by controlling the flow through the valve based on detected data from pressure sensors, which could significantly reduce the effect of fibrosis and also reduce or eliminate other issues related to blebs and bleb management.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A selectable IOP valve for implantation in an eye of a patient, comprising:
   a flow control valve system configured to control flow rates of aqueous, the valve system comprising:
   a plurality of flow control pathways arranged to operate in parallel with each other, each of the flow control pathways being in communication with an entry port to the valve system,
   a flow control mechanism associated with each of the plurality of flow control pathways, the flow control mechanism being arranged to selectively control aqueous flow rates through the flow control pathways, and
   a flexible membrane, wherein the flexible membrane is selectively actuatable by the flow control mechanism to occlude at least one of the plurality of flow control pathways to selectively increase or decrease the flow rate of the aqueous through the flow control valve system.

2. The IOP valve of claim 1, further comprising a drainage tube in fluid communication with the flow control valve system, the drainage tube being configured to convey aqueous from an anterior chamber of an eye.

3. The IOP valve of claim 1, wherein the flexible membrane is actuatable in response to pressure differentials.

4. The IOP valve of claim 3, wherein the flow control mechanism comprises a separate flow control mechanism associated with each of the plurality of flow control pathways.

5. The IOP valve of claim 4, further comprising a check valve disposed in at least one of the plurality of flow control pathways.

6. The IOP valve of claim 4, further comprising a check valve disposed in each of the plurality of flow control pathways.

7. The IOP valve of claim 1, wherein the flow control mechanism comprises a single flow control mechanism associated with multiple flow control pathways of the plurality of flow control pathways.

8. The IOP valve of claim 1, wherein the flow control mechanism comprises a separate flow control mechanism associated with each flow control pathway of the plurality of flow control pathways, each of the separate flow control mechanisms comprising a membrane valve.

9. The IOP valve of claim 8, wherein the membrane valve is biased closed to restrict flow through the flow control pathway until an aqueous pressure exceeds the biasing force.

10. The IOP valve of claim 9, wherein the membrane valve actuates in response to a pressure differential from at least two pressures present in the eye.

11. The IOP valve of claim 10, wherein the at least two pressures include the pressure in an anterior chamber, a drainage location, or atmospheric pressure.

12. The IOP valve of claim 11, wherein at least one pressure approximates atmospheric pressure via fluidic communication with a subconjunctival space of the eye.

13. The IOP valve of claim 1, wherein the flow control mechanism comprises a first membrane and a second membrane associated with at least one of the plurality of flow control pathways.

14. The IOP valve of claim 1, wherein each flow control pathway of the plurality of flow control pathways is arranged to provide a different resistance to aqueous flow.

15. The IOP valve of claim 14, comprising a controller configured to adjust the flow control mechanism to change the amount of flow through each of the plurality of flow control pathways and achieve a desired overall flow rate.

16. The IOP valve of claim 1, wherein the flow control mechanism comprises an actuator fluid and bubble generating system configured to generate bubbles by converting at least a portion of the actuator fluid to a gas.

17. The IOP valve of claim 16, wherein the bubble generating system comprises at least two electrodes.

18. The IOP valve of claim 1, further comprising:
   a power source coupled to the flow control valve system; and
   a processor configured to control the flow control valve system to increase and decrease permitted aqueous flow through the valve.

19. The IOP valve of claim 1, further comprising:
   a first pressure sensor located in fluid communication with the anterior chamber of an eye; and
   a second pressure sensor located in a drainage location;
   wherein a difference between readings from the first pressure sensor and the second pressure sensor approximates a pressure differential between the anterior chamber and the drainage location.

20. The IOP valve of claim 19, wherein readings from the first pressure sensor and the second pressure sensor are used to control the flow control mechanism to modify aqueous flow through the valve.

21. The IOP valve of claim 1, further comprising:
   a first pressure sensor located in fluid communication with the anterior chamber of an eye; and
   a remote pressure sensor located remotely from the first pressure sensor such that the remote pressure sensor measures or approximates atmospheric pressure,
   wherein a difference between readings from the first pressure sensor and the remote pressure sensor measures or approximates intraocular pressure.

22. The IOP valve of claim 21, further comprising a controller configured to use readings from the first pressure sensor and the remote pressure sensor to control the flow control mechanism to modify aqueous flow through the valve.

23. The IOP valve of claim 22, wherein the remote pressure sensor is disposable in the subconjunctival space of the eye.

24. The IOP valve of claim 1, further comprising:
   a first pressure sensor located in a drainage location; and
   a remote pressure sensor located remotely from the first pressure sensor such that the remote pressure sensor measures or approximates atmospheric pressure,
   wherein a difference between readings from the first pressure sensor and the remote pressure sensor approximates pressure in the drainage location.

25. The IOP valve of claim 24, further comprising a controller configured to use readings from the first pressure sensor and the remote pressure sensor to control the flow control mechanism to modify aqueous flow through the valve.

26. The IOP valve of claim 24, wherein the remote sensor is disposable in the subconjunctival space of the eye.

27. The flow control valve system of claim 1, comprising a latch structurally arranged to maintain the flow control mechanism at a desired setting.

28. The IOP valve of claim 27, wherein the latch is disposed to secure the flexible membrane in a desired position.

29. The IOP valve of claim 27, comprising a controller configured to control the latch based on detected pressures.

30. The IOP valve of claim 27, wherein the flow control mechanism is a mechanical displacement device.

31. A selectable IOP valve for implantation in an eye of a patient, comprising:
a drainage pathway arranged to carry aqueous from an anterior chamber of an eye;
a first flow control pathway in communication with the drainage pathway;
a second flow control pathway in communication with the drainage pathway the first and second flow control pathways being arranged to carry aqueous in parallel from the drainage pathway; and
a flow control mechanism associated with both the first and second flow control pathways, wherein the flow control mechanism comprises a single membrane configured to be displaced to increase or decrease aqueous flow rates through the first and second flow control pathways, and wherein the membrane intersects an axis of each of the first and second flow control pathways to selectively occlude the flow of the aqueous through an end of the first and second flow control pathways.

32. The IOP valve of claim 31, wherein the first and second flow control pathways are structurally configured to permit substantially the same flow rates of aqueous.

33. The TOP valve of claim 31, wherein the first and second flow control pathways are structurally configured to permit different flow rates of aqueous.

34. A method performed by an IOP control system that drains aqueous from an anterior chamber of the eye to a drainage location of the eye, comprising:
detecting pressure within an anterior chamber of the eye;
detecting pressure at a drainage location of the eye;
determining whether to adjust drainage aqueous flow based on the detected pressures by comparing the detected pressures in both the anterior chamber and the drainage location to pre-established acceptable pressures; and
adjusting drainage aqueous flow from the anterior chamber by adjusting access to at least one of a plurality of parallel flow paths to achieve pressures in both the anterior chamber and the drainage location corresponding to the acceptable pressures, wherein adjusting access to the at least one of a plurality of parallel flow paths includes adjusting a flow control mechanism associated with the plurality of parallel flow paths, the flow control mechanism comprising a flexible membrane configured to be displaced to increase or decrease aqueous flow through the at least one of a plurality of parallel flow paths, the flexible membrane intersecting an axis of each of the plurality of parallel flow paths to selectively occlude the flow of the aqueous through an end of the plurality of parallel flow paths.

35. The method of claim 34, comprising detecting an atmospheric pressure reference, and wherein the step of determining whether to adjust drainage aqueous flow includes comparing the detected pressure in the anterior chamber and the atmospheric pressure reference.

36. The method of claim 35, wherein the step of detecting an atmospheric pressure reference includes detecting pressure with a sensor located under the conjunctiva of the eye.

37. The method of claim 34, comprising detecting an atmospheric pressure reference, and wherein the step of determining whether to adjust drainage aqueous flow includes comparing the detected pressure in a drainage location and the atmospheric pressure reference.

38. The method of claim 37, wherein the step of detecting an atmospheric pressure reference includes detecting pressure with a sensor located under the conjunctiva of the eye.

39. The method of claim 34, wherein adjusting drainage aqueous flow comprises controlling access to an array of substantially identical parallel flow pathways.

40. The method of claim 34, wherein adjusting drainage aqueous flow comprises controlling access to a plurality of flow pathways arranged in parallel, where each flow pathway of the plurality of flow pathways is structurally configured to permit a different rate of aqueous flow in response to a given driving pressure differential along the flow pathway.

41. The method of claim 34, wherein adjusting access to one of a plurality of parallel flow paths includes displacing a flexible membrane to modify a flow area.

42. The method of claim 41, further comprising mechanically securing the flexible membrane at a desired displacement to maintain a desired flow setting.

43. The method of claim 41, wherein displacing a flexible membrane to modify a flow area comprises using electrolysis to modify a pressure acting on the flexible membrane.

44. The IOP valve of claim 41, wherein the step of displacing a flexible membrane occurs when an aqueous pressure exceeds a biasing force.

* * * * *